United States Patent [19]

Bourdon

[11] 4,351,969
[45] Sep. 28, 1982

[54] PREPARATION OF CHLOROPHENOLS

[75] Inventor: Jacques Bourdon, Saint-Auban, France

[73] Assignee: Rhone-Poulenc Industries, Paris, France

[21] Appl. No.: 244,688

[22] Filed: Mar. 17, 1981

[30] Foreign Application Priority Data

Mar. 17, 1980 [FR] France ................ 80 05876

[51] Int. Cl.³ .......................................... C07C 39/27
[52] U.S. Cl. ..................................................... 568/774
[58] Field of Search ............................. 568/774, 716

[56] References Cited

U.S. PATENT DOCUMENTS 3,532,740 10/1970 Hargls ............................ 585/653
3,660,505 5/1972 Starnes ........................... 568/743

FOREIGN PATENT DOCUMENTS 64426 10/1891 Fed. Rep. of Germany .
2002799 3/1969 France .
2079575 10/1971 France .
2125280 9/1972 France .
2285355 3/1976 France .
7509917 3/1976 Netherlands .

OTHER PUBLICATIONS

"Acta Chemica Scandinavia", vol. 4, pp. 200-204 (1950), Hassel et al.
"J. Amer. Chem. Soc.", vol. 75, pp. 2633-2635 (1953), Berlinger et al.
"Chem. Abstract", vol. 89, p. 127,172z (1978), Pudivol et al.

*Primary Examiner*—Werren B. Lone
*Attorney, Agent, or Firm*—Burns, Doane, Swecker & Mathis

[57] ABSTRACT

Chlorophenols are prepared by thermally dehydrochlorinating a corresponding chlorocyclohexanone in the presence of a catalyst having the formula:

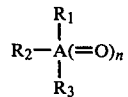

wherein A is phosphorus or arsenic, $R_1$ and $R_2$, which are identical or different, are each hydrogen, an alkyl radical having from 1 to 12 carbon atoms, a phenyl radical or a radical $-NR_4R_5$, in which $R_4$ and $R_5$, which are identical or different, are each H or an alkyl radical having from about 1 to 5 carbon atoms, $R_3$ is an alkyl radical having from 1 to 12 carbon atoms, a phenyl radical or a radical $-NR_4R_5$, in which $R_4$ and $R_5$ are as defined above, and n is equal to 0 or 1.

14 Claims, No Drawings

PREPARATION OF CHLOROPHENOLS

BACKGROUND OF THE INVENTION

1. Field of the Invention

The present invention relates to the preparation of chlorophenols, and, more especially, to the preparation of chlorophenols from chlorocyclohexanones.

2. Description of the Prior Art

Chlorocyclohexanone-to-chlorophenol type processes are generically known to this art.

The earliest known process, for example, comprises heating 2,3,5,6-tetrachlorocyclohexanone at a temperature of 260°–270° C. to prepare 2,6-dichlorophenol [*Acta Chemica Scandinavia,* 4, 200-4 (1950)]. However, only very low yields are realized thereby.

Another process is described in French Patent Application No. 72/1,083, published under No. 2,125,280. Same comprises heating 2,2,6,6-tetrachlorocyclohexanone or 2,2,6-trichlorocyclohexanone at a temperature between 100° and 250° C., in the presence of an amine, an amide, a urea or one of their salts with acids, in order to prepare 2,6-dichlorophenol and ortho-chlorophenol, respectively. It is apparent from reading the examples of the aforesaid patent application, and from confirming independent testing, that the best yields are obtained at a temperature of about 200° C.

Although this second process makes it possible to improve the yield, on the one hand, and to substantially lower the reaction temperature, on the other hand, compared with the first process, it is thus apparent that serious need exists in this art for a process which could be carried out at lower temperatures and at a faster rate than those of the prior art, while suffering no diminution in yields.

See also Beringer et al, *JACS,* 71, pp. 2633–2635 (1953); *Chemical Abstracts,* 89, No. 15, p. 559, item 129172z (1978); U.S. Pat. Nos. 3,532,740 and 3,660,505; Pudovik et al, *Izv. Akad. Nauk SSSR,* Ser. Khim., (7), 1660-1 (1978); West German Pat. No. 64,426; Dutch published application No. 75 09 917; and published French applications Nos. 2,002,799, 2,079,575 and 2,285,355.

SUMMARY OF THE INVENTION

Accordingly, a major object of the present invention is the provision of an improved process for the preparation of chlorophenols, comprising thermally dehydrochlorinating a chlorocyclohexanone of the general formula:

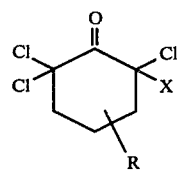

in which X represents a hydrogen atom or a chlorine atom and R represents at least one radical selected from the group comprising H and alkyl radicals having from 1 to 5 carbon atoms, at a temperature above about 120° C., and in the presence of a catalyst of the general formula:

in which A represents phosphorus or arsenic, $R_1$ and $R_2$, which are identical or different, each represents a hydrogen atom or a radical selected from the group comprising alkyl radicals containing from 1 to 12 carbon atoms, phenyl radicals and the radicals:

in which $R_4$ and $R_5$, which are identical or different, each represents H or an alkyl radical having from about 1 to 5 carbon atoms, $R_3$ represents a radical selected from the group comprising alkyl radicals containing from 1 to 12 carbon atoms, phenyl radicals and the radicals:

in which $R_4$ and $R_5$ have the same meaning as above, and n is equal to 0 or 1.

It will also be apparent that the catalyst employed must have a boiling point which is above the temperature at which the reaction is carried out.

DETAILED DESCRIPTION OF THE INVENTION

More particularly according to this invention, $R_1$ and $R_2$, which are identical or different, are preferably a hydrogen atom or a radical selected from the group comprising alkyl radicals having from 1 to 4 carbon atoms and the phenyl radical, and $R_3$ is preferably a radical selected from the group comprising alkyl radicals having from 1 to 4 carbon atoms and the phenyl radical.

The following compounds are exemplary of phosphines and phosphine oxides which are useful within the scope of the present invention: tributylphosphine, triphenylphosphine, diphenylmethylphosphine, diphenylbutylphosphine, diphenylethylphosphine, triphenylphosphine oxide, triethylphosphine oxide, tributylphosphine oxide and hexamethylphosphorotriamide.

According to a particularly preferred embodiment of the invention, triphenylphosphine is the catalyst.

The following compounds are exemplary of arsines and arsine oxides which are useful within the scope of the present invention: diphenylarsine, triphenylarsine, tributylarsine, triphenylarsine oxide and tributylarsine oxide.

According to another particularly preferred embodiment of the invention, triphenylarsine is the catalyst.

The reaction is preferably carried out at a temperature between about 140° C. and about 180° C. More preferably, it is carried out at about 160° C.

It is preferred to use between about 0.1 and about 10% by weight of catalyst, relative to the amount of starting chlorocyclohexanone. Even more preferably, between about 0.5 and about 2% thereof is used.

Although the reaction is preferably carried out under atmospheric pressure, pressures above or below atmospheric pressure are within the ambit of the invention.

The subject reaction is typically carried out in the absence of a solvent medium, but the use of a solvent is also not excluded.

The following compounds are exemplary of starting materials of the formula (I): 2,2,6,6-tetrachlorocyclohexanone, 2,6,6-trichlorocyclohexanone, 4-methyl-2,2,6,6-tetrachlorocyclohexanone and 3-methyl-2,2,6,6-tetrachlorocyclohexanone.

The final products prepared in accordance with the process of the invention have the general formula:

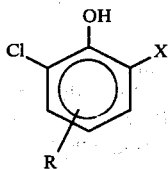

in which X and R are as above defined.

The following compounds are exemplary of those of the formula (III): 2,6-dichlorophenol, orthochlorophenol, 4-methyl-2,6-dichlorophenol and 3-methyl-2,6-dichlorophenol.

The chlorocyclohexanones of the formula (I) are obtained in conventional manner by those skilled in the art, for example, by chlorinating the corresponding cyclohexanone.

In order to further illustrate the present invention and the advantages thereof, the following specific examples are given, it being understood that same are intended only as illustrative and in nowise limitative.

EXAMPLE 1

236 g (1 mol) of 2,2,6,6-tetrachlorocyclohexanone and 2.5 g (0.01 mol) of triphenylphosphine were introduced into a reactor equipped with a stirrer and a condenser. The mixture was heated at 150°–180° C. under stirring; the reaction was terminated when the evolution of hydrogen chloride from the reaction mixture ceased. The reaction mixture was then distilled under reduced pressure (boiling point (20 mm Hg) = 100° C.) to yield 137.5 g of 2,6-dichlorophenol.

Yield of crude 2,6-dichlorophenol = 89.3%.
Yield of distilled 2,6-dichlorophenol = 84.3%.

EXAMPLE 2

190 g (0.8 mol) of 2,2,6,6-tetrachlorocyclohexanone and 3 g (0.065 mol) of triphenylarsine were introduced into the reactor used in Example 1. The reaction mixture was heated at 150°–180° C., under stirring. Same was then treated as in Example 1 to yield 103.4 g of 2,6-dichlorophenol.

Yield of crude 2,6-dichlorophenol = 83.3%.
Yield of distilled 2,6-dichlorophenol = 79.3%.

EXAMPLE 3

118 g (0.5 mol) of 2,2,6,6-tetrachlorocyclohexanone and 1 g (0.006 mol) of hexamethylphosphorotriamide were introduced into the reactor used in Example 1. The reaction mixture was heated at 150°–180° C., under stirring; the reaction was terminated when the evolution of hydrogen chloride from the reaction mixture ceased. The reaction mixture was then distilled under reduced pressure (boiling point (20 mm Hg) = 100° C.) to yield 52 g of 2,6-dichlorophenol.

Yield of 2,6-dichlorophenol = 63.8%.

EXAMPLE 4

222 g (1.1 mols) of 2,2,6-trichlorocyclohexanone and 2.5 g (0.01 mol) of triphenylphosphine were introduced into the reactor used in Example 1. The reaction mixture was heated at 175° C., under stirring; the reaction was terminated when the evolution of hydrogen chloride from the reaction mixture ceased. The reaction mixture was then distilled under reduced pressure (boiling point (10 mm Hg) = 55° C.) to yield 106 g of 2-chlorophenol.

Yield of 2-chlorophenol = 75%.

EXAMPLE 5

120 g (0.48 mol) of 2,2,6,6-tetrachloro-4-methylcyclohexanone and 2 g (0.008 mol) of triphenylphosphine were introduced into the reactor used in Example 1. The reaction mixture was heated at 160°–170° C., under stirring; the reaction was terminated when the evolution of hydrogen chloride from the reaction mixture ceased. The reaction mixture was distilled under reduced pressure to yield 49 g of 2,6-dichloro-4-methylphenol.

Yield of 2,6-dichloro-4-methylphenol = 57.7%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a chlorophenol having the structural formula:

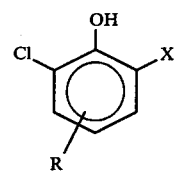

wherein X is hydrogen or chlorine and R is hydrogen or lower alkyl, comprising thermally dehydrochlorinating, at a temperature in excess of about 120° C., a chlorocyclohexanone having the structural formula:

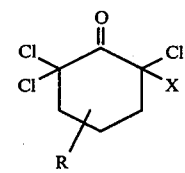

wherein X and R are as above defined, in the presence of a catalytically effective amount of a catalyst having the formula:

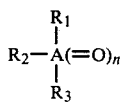

wherein A is phosphorus or arsenic, $R_1$ and $R_2$, which are identical or different, are each hydrogen, an alkyl radical having from 1 to 12 carbon atoms, a phenyl radical or a radical —$NR_4R_5$, in which $R_4$ and $R_5$, which are identical or different, are each H or an alkyl radical having from about 1 to 5 carbon atoms, $R_3$ is an alkyl radical having from 1 to 12 carbon atoms, a phenyl radical or a radical —$NR_4R_5$, in which $R_4$ and $R_5$ are as defined above, and n is equal to 0 or 1.

2. The process as defined by claim 1, wherein the catalyst (II), A is phosphorus.

3. The process as defined by claim 1, wherein the catalyst (II), A is arsenic.

4. The process as defined by claims 2 or 3, wherein the catalyst (II), $R_1$ and $R_2$, which are identical or different, are each hydrogen, an alkyl radical having from 1 to 4 carbon atoms or a phenyl radical, and $R_3$ is an alkyl radical having from 1 to 4 carbon atoms or a phenyl radical.

5. The process as defined by claim 4, wherein the catalyst (III) is triphenylphosphine.

6. The process as defined by claim 4, wherein the catalyst (II) is triphenylarsine.

7. The process as defined by claim 4, wherein the amount present of the catalyst (II) ranges from about 0.1 to about 10% by weight of the chlorocyclohexanone (I).

8. The process as defined by claim 7, said amount present of the catalyst (II) ranging from about 0.5% to about 2%.

9. The process as defined by claims 2 or 3, wherein the chlorocyclohexanone (I) is decomposed at a temperature of from about 140° to about 180° C.

10. The process as defined by claim 9, wherein said decomposition temperature is about 160° C.

11. The process as defined by claims 2 or 3, said chlorocyclohexanone (I) being 2,2,6,6-tetrachlorocyclohexanone.

12. The process as defined by claims 2 or 3, said chlorocyclohexanone (I) being 2,2,6-trichlorocyclohexanone.

13. The process as defined by claim 1, wherein the catalyst (II) is tributylphosphine, diphenylmethylphosphine, diphenylbutylphosphine, diphenylethylphosphine, triphenylphosphine oxide, triethylphosphine oxide, tributylphosphine oxide, hexamethylphosphorotriamide, diphenylarsine, tributylarsine, triphenylarsine oxide or tributylarsine oxide.

14. The process as defined by claims 2 or 3, for the preparation of 2,6-dichlorophenol, ortho-chlorophenol, 4-methyl-2,6-dichlorophenol and 3-methyl-2,6-dichlorophenol.

* * * * *